United States Patent
Joyce et al.

(10) Patent No.: US 9,510,999 B2
(45) Date of Patent: Dec. 6, 2016

(54) MEDICATION DISPENSING PHONE CASE

(71) Applicant: HealthBeacon Limited, Dublin (IE)

(72) Inventors: James Joyce, Dublin (IE); David Shanahan, Brannockstown (IE)

(73) Assignee: Healthbeacon, Inc., Boston, MA (US)

( * ) Notice: Subject to any disclaimer, the term of this patent is extended or adjusted under 35 U.S.C. 154(b) by 0 days.

(21) Appl. No.: 14/819,703

(22) Filed: Aug. 6, 2015

(65) Prior Publication Data

US 2016/0081882 A1    Mar. 24, 2016

Related U.S. Application Data

(60) Provisional application No. 62/033,947, filed on Aug. 6, 2014.

(51) Int. Cl.
| | |
|---|---|
| G08B 23/00 | (2006.01) |
| A61J 7/00 | (2006.01) |
| A61J 1/03 | (2006.01) |
| G06F 19/00 | (2011.01) |
| G08B 21/24 | (2006.01) |

(52) U.S. Cl.
CPC .............. *A61J 7/0076* (2013.01); *A61J 1/03* (2013.01); *G06F 19/3462* (2013.01); *G08B 21/24* (2013.01); *A61J 2200/30* (2013.01); *A61J 2205/60* (2013.01)

(58) Field of Classification Search
CPC ...................................... A61J 7/0076
USPC ...................................... 340/573.1
See application file for complete search history.

(56) References Cited

U.S. PATENT DOCUMENTS

| | | | |
|---|---|---|---|
| 6,603,401 B1* | 8/2003 | Ueyama | A61B 5/0002 340/286.07 |
| 8,639,288 B1* | 1/2014 | Friedman | A61M 5/20 455/556.1 |
| 9,138,539 B1* | 9/2015 | Friedman | A61M 5/20 |
| 9,161,885 B1* | 10/2015 | Zhou | A61J 7/0418 |
| 2007/0097792 A1 | 5/2007 | Burrows et al. | |
| 2011/0181422 A1* | 7/2011 | Tran | G06F 19/3418 340/573.1 |
| 2012/0160716 A1* | 6/2012 | Chan | A61J 7/0481 206/216 |

(Continued)

FOREIGN PATENT DOCUMENTS

WO      2014015293 A1      1/2014

OTHER PUBLICATIONS

Notification of Transmittal of the International Search Report and the Written Opinion of the International Searching Authority for PCT/US2015/43944, "Medication Dispensing Phone Case", date of mailing Jan. 7, 2016.

*Primary Examiner* — Santiago Garcia
(74) *Attorney, Agent, or Firm* — Chapin Intellectual Property Law, LLC

(57) ABSTRACT

A system includes a smartphone contained within a medication adherence case, the medication adherence case including a repository and a hinged access door to the repository, a wireless network linking the smartphone to a content data network (CDN), the CDN including a medication adherence server, and an application residing in the smartphone that sends data to a medical adherence process in the medical adherence server upon receiving a signal generated from a communication device residing in the hinged access door that indicates the hinged access door has been opened.

14 Claims, 3 Drawing Sheets

(56) References Cited

U.S. PATENT DOCUMENTS

| | | | |
|---|---|---|---|
| 2013/0195326 A1* | 8/2013 | Bear | A61J 7/0076 382/128 |
| 2014/0081649 A1* | 3/2014 | Langdon | A61J 1/14 705/2 |
| 2014/0207537 A1* | 7/2014 | Joyce | G07C 13/00 705/12 |
| 2014/0374294 A1* | 12/2014 | Joyce | G06F 19/3456 206/363 |
| 2015/0269825 A1* | 9/2015 | Tran | G08B 21/0446 340/539.12 |
| 2016/0034669 A1* | 2/2016 | Mahbubian | G05B 15/02 700/232 |
| 2016/0143807 A1* | 5/2016 | Ika | A61J 1/03 206/216 |

\* cited by examiner

MEDICATION DISPENSING PHONE CASE

CROSS REFERENCE TO RELATED APPLICATION

This application claims priority from U.S. Provisional Patent Application Ser. No. 62/033,947, filed Aug. 6, 2014, the entire contents of which are incorporated herein.

BACKGROUND OF THE INVENTION

The present invention generally relates to medical adherence, and more specifically to a medication dispensing phone case.

In general, medication adherence usually refers to whether patients take their medications as prescribed (e.g., twice daily), as well as whether they continue to take a prescribed medication. Medication non-adherence is a growing concern to clinicians, healthcare systems, and other stakeholders (e.g., payers) because of mounting evidence that it is prevalent and associated with adverse outcomes and higher costs of health care. To date, measurement of patient medication adherence and use of interventions to improve adherence are rare in routine clinical practice.

SUMMARY OF THE INVENTION

The following presents a simplified summary of the innovation described herein. This summary is not an extensive overview of the invention. It is intended to neither identify key nor critical elements of the invention nor delineate the scope of the invention. Its sole purpose is to present some concepts of the invention in a simplified form as a prelude to the more detailed description that is presented later.

The present invention relates generally to medical adherence, and more specifically to a medication dispensing phone case.

In one aspect, the invention features a system including a smartphone contained within a medication adherence case, the medication adherence case including a repository and a hinged access door to the repository, a wireless network linking the smartphone to a content data network (CDN), the CDN including a medication adherence server, and an application residing in the smartphone that sends data to a medical adherence process in the medical adherence server upon receiving a signal generated from a communication device residing in the hinged access door that indicates the hinged access door has been opened.

In another aspect, the invention features a system including a smartphone contained within a medication adherence case, the medication adherence case including a repository and a rotary dispensing device, and a sensor in the rotary dispensing device configured to detect a movement of the rotary dispensing device and send a signal to an application residing in the smartphone that indicates the rotary dispensing device has been rotated.

In another aspect, the invention features a system including a smartphone contained within a medication adherence case, the medication adherence case including a syringe repository and a dispensing device to the syringe repository, the dispensing device comprising at least a release button and a release door, and a sensor in the release door configured to detect a movement of the release door and send a signal to an application residing in the smartphone indicating that the release door has been opened or closed.

In another aspect, the invention features a system including a smartphone contained within a medication adherence case, the medication adherence case including a liquid repository and a control valve attached to the liquid repository, and a sensor in the control valve configured to detect a movement of liquid from the liquid repository through control valve and send a signal to an application residing in the smartphone.

In another aspect, the invention features a method including, in a smartphone comprising at least a display, a processor and a memory, displaying a medicine delivery alert on a smartphone, receiving a signal indicative of a medicine delivery, the signal originating from communication device in an opening in a repository contained in a smartphone case enclosing the smartphone, storing a record including a time stamp of the signal along with other information, and sending the record to a server residing in a content data network for processing the received record.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The features and advantages of the invention are apparent from the following description taken in conjunction with the accompanying drawings in which.

DETAILED DESCRIPTION OF THE INVENTION

Figure 1:
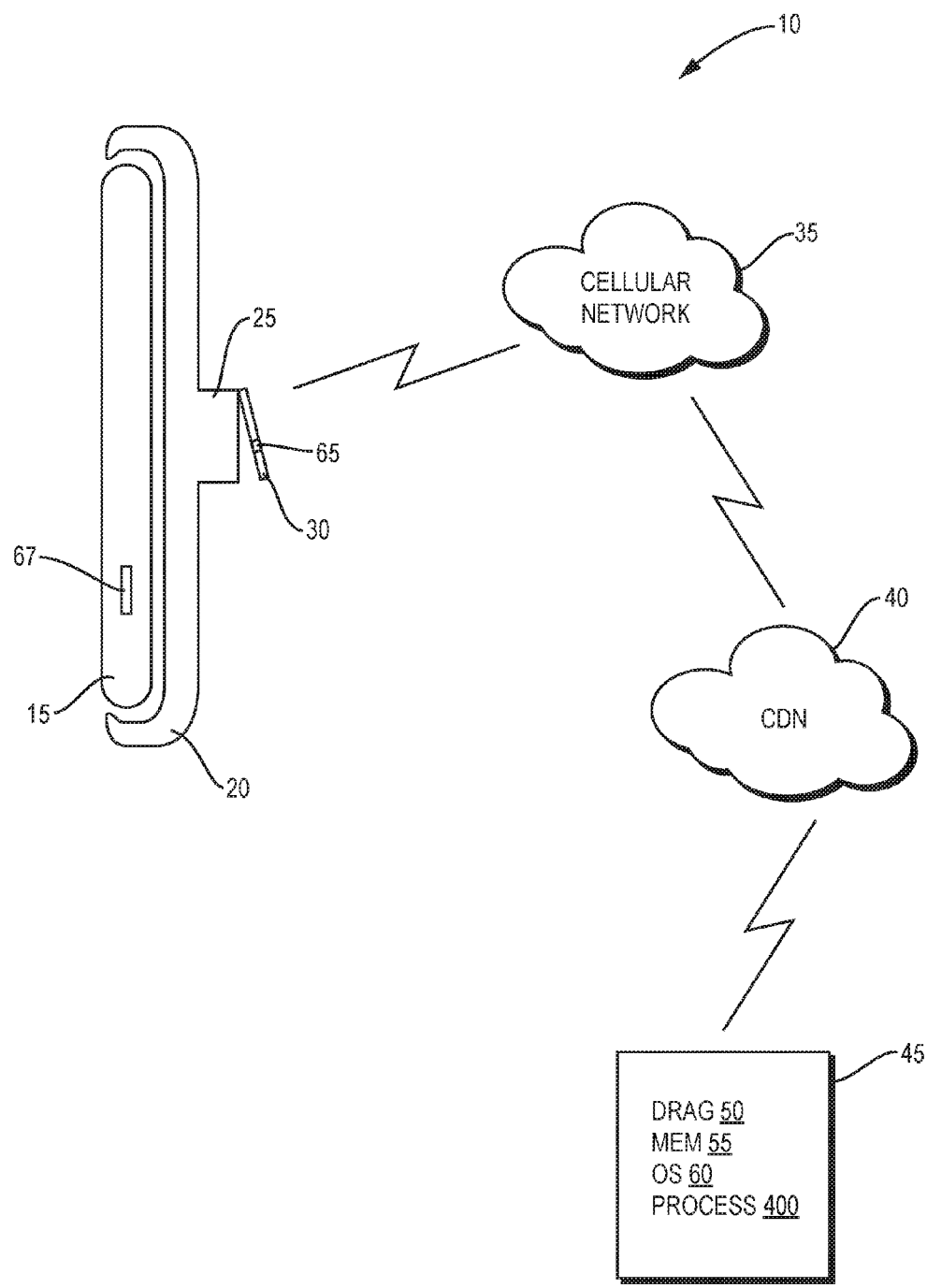
FIG. 1 is an illustration of a first embodiment of an exemplary medication adherence system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Medication adherence one of the most significant health challenges of modern healthcare systems. Patients must be motivated to take their medications, have easy access to them, and critically remember when to take them. At the same time, smart phones (i.e., a cellular phone that is able to perform many of the functions of a computer, typically having a relatively large screen and an operating system capable of running general-purpose applications) have changed how we communicate, remember events, and are often with us throughout the day. The present invention is a connected medical dispensing case that encases a smart phone, while dispensing a user's medication.

As shown in FIG. 1, a first embodiment of an exemplary medication adherence system 10 includes a smartphone 15 contained within an exemplary medication adherence case 20. The medication adherence case 20, which may be fabricated from any suitable protective material, such as a polymeric or solid material, includes a repository 25 (e.g., pillbox) and a hinged access door 30. In the embodiment shown in FIG. 1, the repository 25 is designed to house a store of solid medicine in the form of pills.

The medication adherence system 10 also includes a cellular network 35 linked to a content data network (CDN) 40. The CDN includes a medication adherence server 45. The medical adherence server 45 includes a processor 50 and memory 55. The memory 55 includes at least an operating system 60, such as Windows or Linux, and a medication adherence process 400, described below.

The hinged access door includes a communications device 65 that is in communication with an application (app) 67 residing within a memory of the smartphone 15. The communications device 65 may use one of any communications technologies to interact with the app 67 in the smartphone, such as Near Field Communications (NFC), Radio Frequency Identification (RFID) or local area wireless communication (WiFi), and a sensor enabled to detect a movement of the hinged access door 30.

When the hinged access door 30 is opened, the sensor detects the movement and the communications device 65 sends a signal to the app 67 residing in the smartphone indicating the hinged access door 30 opening. When the hinged access door 30 is closed after being opened, the sensor detects the movement and the communications device 35 sends a signal to the app 67 residing in the smartphone indicating the hinged access door 30 closing. The actions of the hinged access door 30 opening and closing as detected by the sensor are recorded in the memory of the smart phone 15, along with additional information, indicating a dispensing of one or more pills residing in the repository 25. The additional information may include one or more of a date, time, physical activity, user heart rate, and so forth.

The app 67 may be programmed to generate a reminder indication to a user that it is time to take a pill in the repository 25. The indication can include an auditory and/or visual que. In embodiments, the app 67 may present an interactive graphical user interface (GUI) to a user that enables setting reminder alerts, for example.

Once a pill is dispensed, the app 67 may store and/or periodically communicate the actions of the hinged access door 30 and/or the additional information from the smartphone 15 to medication adherence process 400 through the cellular network 35 and CDN 40. These actions enable the medication adherence process 400 to track whether a patient has taken their medicine and a level of compliance. Further, the information of when a patient takes their medication can then be analyzed to understand and gain insight into their personal medical adherence and general patient behavior. In addition, reports can be generated by the medication adherence process 400 and reminders sent to the smartphone 15 via, for example, email or SMS text message, indicating lack of adherence or compliance with adherence. These messages can serve to re-enforce a user's compliance and behavior.

Figure 2:
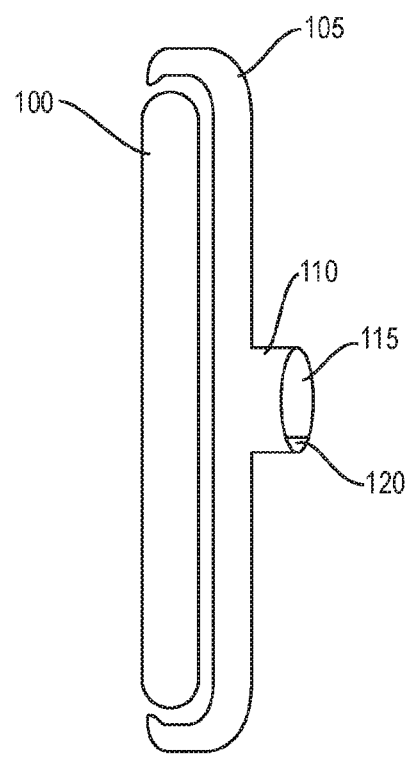
FIG. 2 is an illustration of a second embodiment of a smartphone including an exemplary medication adherence case.

As shown in FIG. 2, a second embodiment includes a smartphone 100 including an exemplary medication adherence case 105 having a repository 110 and a rotary dispensing device 115. Here again, the repository 110 is designed to house a store of solid medicine in the form of pills. The rotary dispensing device 115 delivers a single pill from the repository 110 when rotated. A sensor 120 contained in the rotary dispensing device 115 detects rotation and signals the app 67 via a communications technology such as, for example, Near Field Communications (NFC), Radio Frequency Identification (RFID) or local area wireless communication (WiFi).

Here again, once a pill is dispensed as indicated by the sensor 120, the app 67 may store and/or periodically communicate the actions and/or the additional information from the smartphone 15 to medication adherence process 400 through the cellular network 35 and CDN 40.

Figure 3:
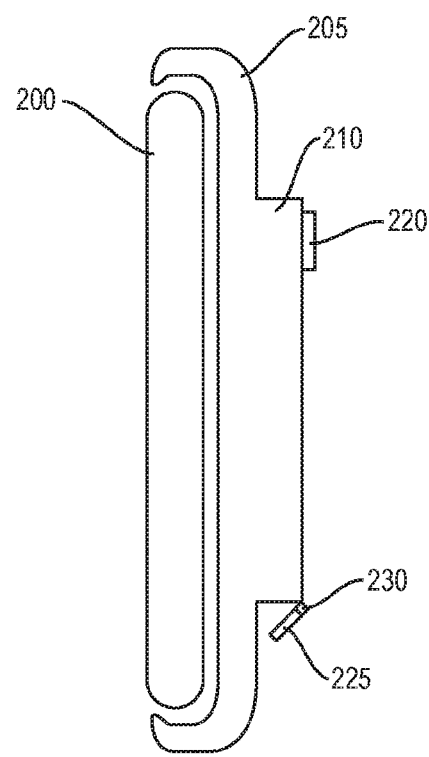
FIG. 3 is an illustration of a third embodiment of a smartphone including an exemplary medication adherence case.

As shown in FIG. 3, a third embodiment includes a smartphone 200 including an exemplary medication adherence case 205 having a repository 210 and a dispensing device 215. In this embodiment, the repository 210 includes disposable syringes and the dispensing device 215 includes a release button 220 and a release door 225. Pressing the release button 220 opens the release door 225, delivering one disposable syringe from the repository 210. The release door 225 includes a sensor 230 configured to detect the release door 225 opening and closing. Each time the release door 22 is opened, the sensor 230 sends a signal to the app 67. In the example, the app 67 may be configured to alert a user via a visual and/or audible indicator that it is time to press the release button 220 to open the release door 225 to obtain a disposable syringe from the repository 210.

Once again, once a syringe is dispensed as indicated by the sensor 230, the app 67 may store and/or periodically communicate the actions and/or the additional information from the smartphone 15 to medication adherence process 400 through the cellular network 35 and CDN 40.

Figure 4:
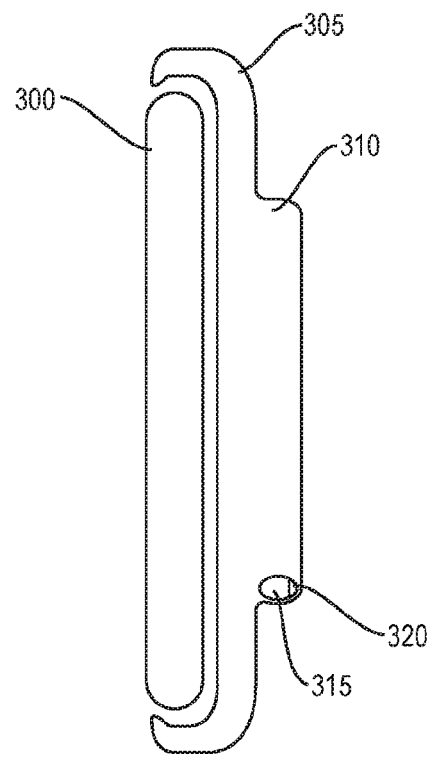
FIG. 4 is an illustration of a fourth embodiment of a smartphone including an exemplary medication adherence case.

As shown in FIG. 4, a fourth embodiment includes a smartphone 300 including an exemplary medication adherence case 305 having a repository 310 configured to contain a liquid medicine. The repository 310 includes a one-way valve 315 that enables the liquid medicine to be metered out from the repository 310 when the repository 310 is squeezed by a user. The one-way valve 315 includes a sensor 320 configured to detect a fluid flow. Each time the liquid medicine flows through the one-way valve 315 the sensor 320 sends a signal of the event to the app 67. Once the liquid is dispensed as indicated by the sensor 320, the app 67 may store and/or periodically communicate the actions and/or the additional information from the smartphone 15 to medication adherence process 400 through the cellular network 35 and CDN 40.

Other embodiments may include an epinephrine containing a smartphone case with a sequestered epi-syringe and needle enclosed.

Figure 5:
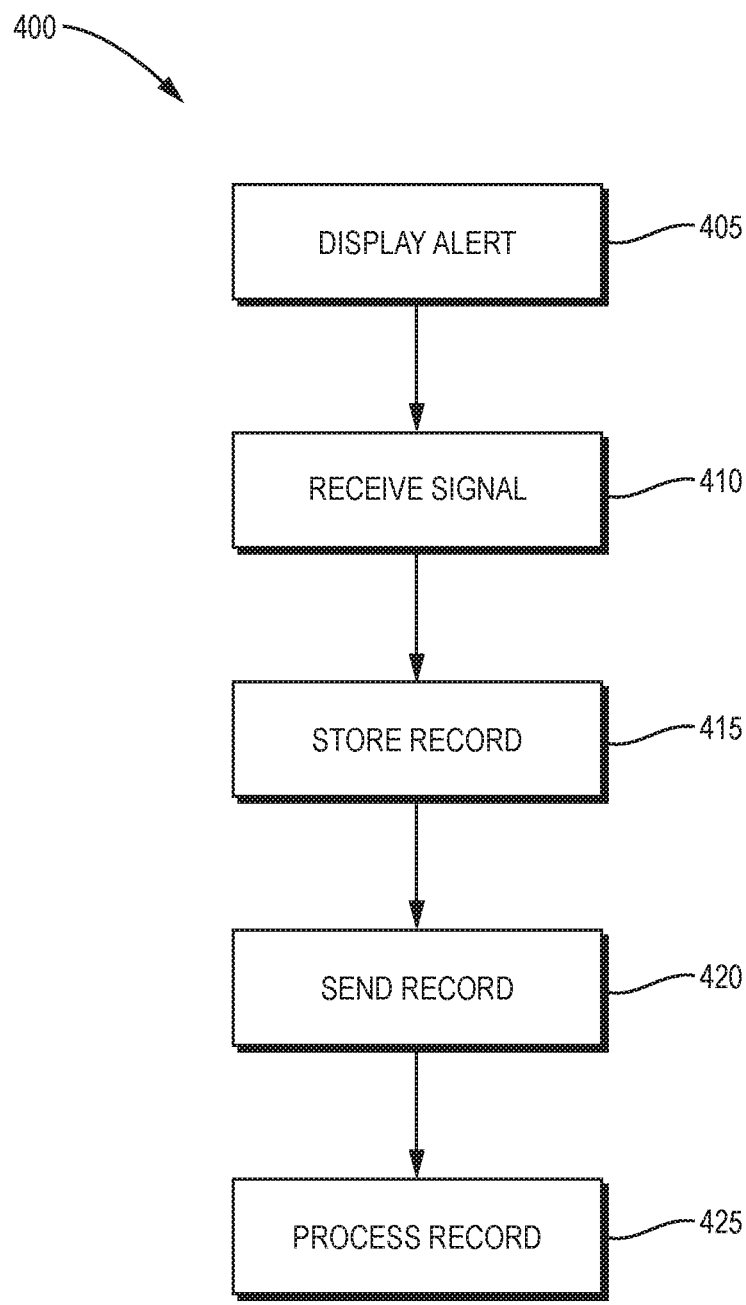
FIG. 5 is a flow diagram.

As shown in FIG. 5, medication adherence process 400 includes displaying (405) a medicine delivery alert on a smartphone.

Process receives (410) a signal indicative of a medicine delivery, the signal originating from an opening in a repository contained in a smartphone case enclosing the smartphone.

Process 400 stores (415) a record including a time stamp of the signal along with other information.

Process 400 sends (420) the record to a server residing in a content data network.

Process 440 processes (430) the received record.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. Accordingly, any apparently limiting statements are made only with regard to a particular embodiment, and are not limiting of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system comprising:
    a smartphone contained within a medication adherence case, the medication adherence case including a repository and a hinged access door to the repository;
    a wireless network linking the smartphone to a content data network (CDN), the CDN including a medication adherence server; and an application residing in the smartphone that sends data to a medical adherence process in the medical adherence server upon receiving a signal generated from a communication device residing in the hinged access door that indicates the hinged access door to the repository of the medical adherence case has been opened, the medical adherence process sending a signal to the application residing in the smartphone in response.

2. The system of claim 1 wherein the communications device comprises a sensor configured to detect an opening and a closing of the hinged access door.

3. The system of claim 2 wherein the signal is a Near Field Communications (NFC), Radio Frequency Identification (RFID) signal or local area wireless communication (WiFi) signal.

4. The system of claim 1 wherein the medication adherence case is fabricated from a protective material.

5. The system of claim 1 wherein the repository is configured to house a store of pills.

6. The system of claim 1 wherein the data comprises one or more of a date, a time, a physical activity, and a user heart rate.

7. The system of claim 1 wherein the application residing in the smartphone generates periods reminders to a user of the smartphone.

8. The system of claim 1 wherein the medical adherence process analyzes the data and generates one or more reports.

9. A system comprising:
    a smartphone contained within a medication adherence case, the medication adherence case including a repository and a rotary dispensing device; and
    a sensor in the rotary dispensing device configured to detect a movement of the rotary dispensing device of the medication adherence case and send a signal to an application residing in the smartphone that indicates the rotary dispensing device of the medication adherence case has been rotated, the application residing in the smartphone sending data to a medical adherence process in a medical adherence server upon receiving the signal, the medical adherence process sending a signal to the application residing in the smartphone in response.

10. The system of claim 9 when the movement of the rotary dispensing device dispenses a single pill.

11. A system comprising:
    a smartphone contained within a medication adherence case, the medication adherence case including a liquid repository and a control valve attached to the liquid repository; and a sensor in the control valve configured to detect a movement of liquid from the liquid repository through the control valve and send a signal to an application residing in the smartphone when liquid moves from the liquid repository through the control valve, the application residing in the smartphone sending data to a medical adherence process in a medical adherence server upon receiving the signal, the medical adherence process sending a signal to the application residing in the smartphone in response.

12. A method comprising:
    in a smartphone comprising at least a display, a processor and a memory, displaying a medicine delivery alert on a smartphone;
    receiving a signal indicative of a medicine delivery, the signal originating from communication device in an opening in a repository contained in a smartphone case enclosing the smartphone;
    storing a record including a time stamp of the signal indicative of the medicine delivery along with other information; and
    sending the record to a server residing in a content data network for processing the received record, the server sending a signal to the smartphone in response, wherein the processing comprises analyzing and generating reports indicating lack of adherence or compliance with adherence.

13. The method of claim 12 wherein the medicine delivery is selected from the group consisting of a pill, a liquid and a syringe.

14. The method of claim 12 wherein the opening is to one of a pill repository, a rotary dispensing device or a liquid repository.

* * * * *